(12) United States Patent
Akerbald et al.

(10) Patent No.: US 7,267,953 B2
(45) Date of Patent: Sep. 11, 2007

(54) METHOD FOR IDENTIFICATION OF MODULATORS OF PRE-ADIPOCYTE DIFFERENTIATION

(75) Inventors: Peter Akerbald, Mölndal (SE); Mikael Sigvardsson, Lund (SE)

(73) Assignee: AstraZeneca AB, Sodertajle (SE)

( * ) Notice: Subject to any disclaimer, the term of this patent is extended or adjusted under 35 U.S.C. 154(b) by 0 days.

(21) Appl. No.: 10/491,643

(22) PCT Filed: Oct. 3, 2002

(86) PCT No.: PCT/GB02/04479

§ 371 (c)(1),
(2), (4) Date: Jan. 13, 2005

(87) PCT Pub. No.: WO03/031985

PCT Pub. Date: Apr. 17, 2003

(65) Prior Publication Data

US 2005/0123915 A1    Jun. 9, 2005

(30) Foreign Application Priority Data

Oct. 5, 2001  (GB) ................. 0123962.3
Jun. 27, 2002 (GB) ................. 0214814.6

(51) Int. Cl.
*C12Q 1/68* (2006.01)
(52) U.S. Cl. .......................... 435/6; 530/350
(58) Field of Classification Search ............ None
See application file for complete search history.

(56) References Cited

FOREIGN PATENT DOCUMENTS

| EP | 1158044 A1 | 2/2000 |
|----|------------|--------|
| WO | WO-00/44882 A2 | 8/2000 |
| WO | WO-00/46348 A1 | 8/2000 |
| WO | WO-01/64238 A2 | 9/2001 |

OTHER PUBLICATIONS

Dowell et al., "Olf-1/Early B Cell Factor is a Regulator of *glut4* Gene Expression in 3T3-L1 Adipocytes," The Journal of Biological Chemistry 277(3):1712-1718 (2002).

Milatovich et al., "Gene for a Tissue-specific Transcriptional Activator (EBF or OLF-1), Expressed iin Early B Lymphocytes, Adipocytes, and Olfactor Neurons, is Located on Human Chromosome 5, Band q34, and Proximal Mouse Chromosome 11," Mammalian Genome 5:211-215 (1994).

Hagman et al., "EBF Contains a Novel Zinc Coordination Mofit and Multiple Dimerization and Transcriptional Activation Domains," The Embo Journal 14(12):2907-2916 (1995).

*Primary Examiner*—James Ketter

(57) ABSTRACT

The invention relates to a method for identification of a compound which modulates pre-adipocyte differentiation comprising testing whether the compound modulates the activity and/or amount of O/E-1 and/or O/E-2 and/or O/E-3. The invention also relates to use of a compound able to modulate the activity or amount of O/E-1 and/or O/E-2 and/or O/E-3 in preparation of a medicament for the treatment or prevention of atherosclerosis, dyslipidemia, IRS, and type 2 diabetes.

14 Claims, 11 Drawing Sheets

Vector              O/E-1

SEQUENCE LISTING

<160> NUMBER OF SEQ ID NOS: 20

<210> SEQ ID NO 1
<211> LENGTH: 24
<212> TYPE: DNA
<213> ORGANISM: Artificial Sequence
<220> FEATURE:
<223> OTHER INFORMATION: PCR Forward Primer mEBF1 fw

```
<400> SEQUENCE: 1
aggttggatt ctgctacgaa agtt                                          24

<210> SEQ ID NO 2
<211> LENGTH: 23
<212> TYPE: DNA
<213> ORGANISM: Artificial Sequence
<220> FEATURE:
<223> OTHER INFORMATION: PCR Reverse Primer mEBF1 rev

<400> SEQUENCE: 2
tgattcctct taaaaaggcc tga                                           23

<210> SEQ ID NO 3
<211> LENGTH: 25
<212> TYPE: DNA
<213> ORGANISM: Artificial Sequence
<220> FEATURE:
<223> OTHER INFORMATION: PCR Forward Primer mEBF2 fw

<400> SEQUENCE: 3
agcacaaaac tacttattcc gatgg                                         25

<210> SEQ ID NO 4
<211> LENGTH: 18
<212> TYPE: DNA
<213> ORGANISM: Artificial Sequence
<220> FEATURE:
<223> OTHER INFORMATION: PCR Reverse Primer mEBF2 rev

<400> SEQUENCE: 4
gtccaacatg gccgcttg                                                 18

<210> SEQ ID NO 5
<211> LENGTH: 21
<212> TYPE: DNA
<213> ORGANISM: Artificial Sequence
<220> FEATURE:
<223> OTHER INFORMATION: PCR Forward Primer mEBF3 fw

<400> SEQUENCE: 5
tcgtgaatat gcaccgtttt g                                             21

<210> SEQ ID NO 6
<211> LENGTH: 26
<212> TYPE: DNA
<213> ORGANISM: Artificial Sequence
<220> FEATURE:
<223> OTHER INFORMATION: PCR Reverse Primer mEBF3 rev

<400> SEQUENCE: 6
atgagtacag aaaaaatgtc tcgagg                                        26

<210> SEQ ID NO 7
<211> LENGTH: 19
<212> TYPE: DNA
<213> ORGANISM: Artificial Sequence
<220> FEATURE:
<223> OTHER INFORMATION: PCR Forward Primer mSREBP1 fw

<400> SEQUENCE: 7
gcagaccctg gtgagtgga                                                19

<210> SEQ ID NO 8
```

-continued

```
<211> LENGTH: 19
<212> TYPE: DNA
<213> ORGANISM: Artificial Sequence
<220> FEATURE:
<223> OTHER INFORMATION: PCR Reverse Primer mSREBP1 rev

<400> SEQUENCE: 8
gtcggtggat gggcagttt                                            19

<210> SEQ ID NO 9
<211> LENGTH: 19
<212> TYPE: DNA
<213> ORGANISM: Artificial Sequence
<220> FEATURE:
<223> OTHER INFORMATION: PCR Forward Primer mC/EBP? fw

<400> SEQUENCE: 9
tctgcgagca cgagacgtc                                            19

<210> SEQ ID NO 10
<211> LENGTH: 20
<212> TYPE: DNA
<213> ORGANISM: Artificial Sequence
<220> FEATURE:
<223> OTHER INFORMATION: PCR Reverse Primer mC/EBP? rev

<400> SEQUENCE: 10
gccaggaact cgtcgttgaa                                           20

<210> SEQ ID NO 11
<211> LENGTH: 20
<212> TYPE: DNA
<213> ORGANISM: Artificial Sequence
<220> FEATURE:
<223> OTHER INFORMATION: PCR Forward Primer mALBP fw

<400> SEQUENCE: 11
ttcgatgaaa tcaccgcaga                                           20

<210> SEQ ID NO 12
<211> LENGTH: 15
<212> TYPE: DNA
<213> ORGANISM: Artificial Sequence
<220> FEATURE:
<223> OTHER INFORMATION: PCR Reverse Primer mALBP rev

<400> SEQUENCE: 12
agggccccgc catct                                                15

<210> SEQ ID NO 13
<211> LENGTH: 22
<212> TYPE: DNA
<213> ORGANISM: Artificial Sequence
<220> FEATURE:
<223> OTHER INFORMATION: PCR Forward Primer mGPDH fw

<400> SEQUENCE: 13
tgctaaatgg gcagaagcta ca                                        22

<210> SEQ ID NO 14
<211> LENGTH: 21
<212> TYPE: DNA
<213> ORGANISM: Artificial Sequence
<220> FEATURE:
<223> OTHER INFORMATION: PCR Reverse Primer mGPDH rev

<400> SEQUENCE: 14
```
tgtgttggag aatgctgtgc a					21

<210> SEQ ID NO 15
<211> LENGTH: 18
<212> TYPE: DNA
<213> ORGANISM: Artificial Sequence
<220> FEATURE:
<223> OTHER INFORMATION: PCR Forward Primer mPPAR?2 fw

<400> SEQUENCE: 15
gcatggtgcc ttcgctga					18

<210> SEQ ID NO 16
<211> LENGTH: 22
<212> TYPE: DNA
<213> ORGANISM: Artificial Sequence
<220> FEATURE:
<223> OTHER INFORMATION: PCR Reverse Primer mPPAR?2 rev

<400> SEQUENCE: 16
tggcatctct gtgtcaacca tg					22

<210> SEQ ID NO 17
<211> LENGTH: 22
<212> TYPE: DNA
<213> ORGANISM: Artificial Sequence
<220> FEATURE:
<223> OTHER INFORMATION: PCR Forward Primer mPPAR?1 fw

<400> SEQUENCE: 17
tgaaagaagc ggtgaaccac tg					22

<210> SEQ ID NO 18
<211> LENGTH: 22
<212> TYPE: DNA
<213> ORGANISM: Artificial Sequence
<220> FEATURE:
<223> OTHER INFORMATION: PCR Reverse Primer mPPAR?1 rev

<400> SEQUENCE: 18
tggcatctct gtgtcaacca tg					22

<210> SEQ ID NO 19
<211> LENGTH: 24
<212> TYPE: DNA
<213> ORGANISM: Artificial Sequence
<220> FEATURE:
<223> OTHER INFORMATION: PCR Forward Primer m36b4  fw

<400> SEQUENCE: 19
gaggaatcag atgaggatat ggga					24

<210> SEQ ID NO 20
<211> LENGTH: 20
<212> TYPE: DNA
<213> ORGANISM: Artificial Sequence
<220> FEATURE:
<223> OTHER INFORMATION: PCR Reverse Primer m36b4 rev

<400> SEQUENCE: 20
aagcaggctg acttggttgc					20

METHOD FOR IDENTIFICATION OF MODULATORS OF PRE-ADIPOCYTE DIFFERENTIATION

This application is a national stage filing under 35 U.S.C. 371 of International Application No. PCT/GB02/04479, filed Oct. 3, 2002, which claims priority from United Kingdom Patent Application No. 0123962.3, filed Oct. 5, 2001, and United Kingdom Patent Application No. 0214814.6, filed Jun. 27, 2002, the specifications of which are incorporated by reference herein. International Application No. PCT/GB02/04479 was published under PCT Article 21(2) in English.

The invention relates to methods of screening test compounds for their ability to modulate pre-adipocyte differentiation by measuring their activity as a modulator of O/E-1 and/or O/E-2 and/or O/E-3 activity or expression. The invention also relates to the use of active modulators of O/E-1 and/or O/E-2 and/or O/E-3 activity or expression in stimulation of pre-adipocyte differentiation and hence also in the treatment or prevention of atherosclerosis, or insulin resistance syndrome, or dyslipidemia, or type 2 diabetes. The invention also relates to the use of active modulators of O/E-1 and/or O/E-2 and/or O/E-3 activity or expression in inhibition of pre-adipocyte differentiation and hence also in the treatment or prevention of obesity. The development of cell lineages with specialized phenotypes is essential for all multicellular organisms. Each specific cellular phenotype is determined by the set of genes expressed and this can be regulated by both intrinsic and extrinsic factors. The most studied way of controlling gene expression is through transcriptional regulation. Gain and lack of function experiments have also shown that numerous transcription factors are critical for development of many cell types. For example, the myogenic transcription factors Myf-5, MyoD, myogenin essential for muscle cell development (Massari and Murre (2000) Mol Cell Biol 20, 429-40), the nuclear hormone receptor PPARγ for adipocytes (Rosen et al. (2000) Genes Dev. 14, 1293-307) and the E2A transcription factors for B-lymphocyte differentiation (Liberg and Sigvardsson (1999) Crit Rev Immunol 19, 127-53). The molecular mechanisms controlling the development of adipocytes have been studied extensively through the use of immortalized murine preadipocyte cell lines such as 3T3-L1 and F442A and also by gain of function experiments in NIH/3T3 fibroblasts. These preadipocytes can be induced by hormonal stimulation to differentiate into adipocytes that resemble cells found in white adipose tissue. Using 3T3-L1 as a model system for adipocyte development it has been possible to dissect this process into distinct stages with coordinated expression of specific genes. These include genes important for lipid metabolism and adipocyte function as well as secreted hormones involved in controlling adipocyte differentiation. All these genes are however expressed at later differentiation stages when the mature adipocyte is already formed. Studies of the promoters of these adipocyte specific genes have led to the isolation of several adipocyte differentiating transcription factors such as PPAR, C/EBP and ADD1 that coordinate the development of this cell lineage. (Cowherd et al. (1999) Semin Cell Dev Biol 10, 3-10; Rosen et al. (2000) Genes Dev 14, 1293-307).

EBF (Early B-cell Factor) also called Olfactory factor-1 (Olf-1) or O/E-1 is a 64 kD transcription factor originally described to be important for control of B-lymphocyte specific genes and for transcriptional regulation of genes in olfactory receptor neurons (Hagman et al. (1993) Genes and Development 7, 760-773; Lin and Grosschedl (1995) Nature 376, 263-7; Wang et al. (1997) J Neurosci 17, 4149-58). O/E-1 belongs to the helix loop helix (HLH) family of transcription factors, which includes proteins such as MyoD, E2A, Myc and NeuroD that are important for development and determination of several mammalian cell lineages (Massari and Murre (2000) Mol Cell Biol 20, 429-40). This HLH motif is important for homo- and hetero-dimerization of HLH factors; O/E-1 is however suggested to interact with natural DNA binding sites only as a homodimer (Travis et al. (1993) Mol Cell Biol 13, 3392-3400). O/E-1 differs from other HLH transcription factors in that it besides this dimerization domain also contains a unique zinc coordination motif that mediates DNA binding to a ATTCCCNNGG-GAAT (SEQ ID NO: 21) consensus DNA binding site (Hagman et al. (1995) Embo J 14, 2907-16; Travis et al. (1993) Mol Cell Biol 13, 3392-3400). O/E-1 also contains two transactivation domains, one within the DNA binding domain and one in C-terminal part of the protein that both are important for full transcriptional activity (Hagman et al. (1995) Embo J 14, 2907-16). Many of the characterized target genes for O/E-1 also contains binding sites for E-box binding transcription factors like the E2A proteins and O/E-1 has also been shown to act in synergy with these factors to achieve a high rate of transcription (Sigvardsson et al. (1997) Immunity 7, 25-36). The O/E family has been extremely conserved during evolution and is present in *C. elegans* (Prasad et al. (1998) Development 125, 1561-8), *Drosophila* (Crozatier et al. (1996) Curr Biol 6, 707-18), zebra fish (Bally-Cuif et al. (1998) Mech Dev 77, 85-90) and chicken (Nieminen et al. (2000) Scand J Immunol 52, 465-9), indicating that these proteins and their role have been preserved through selective pressure. In mammals the O/E family of HLH transcription factors contains three highly conserved members: Olf-1/EBF, Olf-1/EBF-like 2 and 3 (O/E-1, -2 and -3) (Wang et al. (1997) J Neurosci 17, 4149-58). In the mouse O/E-1 is expressed in B-lymphocytes, olfactory neurons, cerebellum and adipose tissue, while O/E-2 and -3 are more restricted to olfactory neurons (Hagman et al. (1993) Genes and Development 7, 760-773; Wang et al. (1997) J Neurosci 17, 4149-58). O/E-1 is the best characterized family member and its role in the development of B-lymphocytes has been studied extensively. By promoter analysis several B-lymphocyte specific target genes have been identified that all are involved in forming the pre-B cell receptor and signaling through this complex. Mice made devoid of O/E-1 by homologous recombination do also show a complete lack of B-lymphocytes, which shows that this protein is indeed of great importance for B-lymphocyte development. These mice had however no gross defects in the central nervous system, indicating a redundancy between the O/E proteins in the brain (Lin and Grosschedl (1995) Nature 376, 263-7). All experiments performed so far indicate that O/E-1 seems to play similar roles in B-lymphocytes in humans and mice (Gisler et al. (2000) Blood 96, 1457-64). Roaz is a recently described protein that can interact with O/Es and other transcription factors and function as a negative regulator of transcription suggesting that there are systems available to fine tune the activity of the O/E proteins (Tsai and Reed (1997) J Neurosci 17, 4159-69); Tsai and Reed (1998) Mol Cell Biol 18, 6447-56).

The present invention is based on the discovery that expression of O/E-1 and/or O/E-2 and/or O/E-3 stimulates adipocyte differentiation and development.

The invention relates to the use of a variety of procedures for using O/E-1 and/or O/E-2 and/or O/E-3 in the discovery of modulators of O/E-1 and/or O/E-2 and/or O/E-3 function or expression in modulating pre-adipocyte differentiation and therefore used to ameliorate the dyslipidemia associated with conditions like, but not limited to, the insulin resistance syndrome including type 2 diabetes and obesity and thus ultimately to prevent cardiovascular morbidity and mortality caused by atherosclerosis.

The invention further relates to pharmaceutical compositions containing such a modulator discovered by the methods described in this application and the use of the modulator or pharmaceutical composition comprising such modulator in modulating pre-adipocyte differentiation and therefore used to modify or ameliorate or prevent atherosclerosis or insulin resistance syndrome or dyslipidemia or type 2 diabetes or obesity.

Expression of O/E-1 in NIH/3T3 fibroblasts, 3T3-L1 preadipocytes, or mouse embryonic fibroblasts (MEF) enhances the differentiation of these cells to adipocytes. Expression of O/E-2 and/or O/E-3 in 3T3-L1 preadipocytes enhances the differentiation of these cells to adipocytes. This demonstrates that O/E-1 and/or O/E-2 and/or O/E-3 represents an important regulatory factor in the adipocyte differentiation.

Adipate differentiation is accompanied by the induction of several genes that are involved in lipid metabolism such as the adipocyte fatty acid binding protein (aP2), phosphoenolpyruvate carboxykinase (PEPCK), acyl CoA synthetase (ACS), the fatty acid transporter (FATP-1) and lipoprotein lipase (LPL) as well as genes involved in glucose utilisation such as the insulin dependent glucose transporter GLUT4. Compounds that stimulates the adipocyte differentiating effects of O/E-1 may therefore be useful in the treatment of disease conditions characterised by increased plasma levels of triglycerides, cholesterol, free fatty acids, insulin, glucose and decreased insulin sensitivity. Examples of such diseases are the insulin resistance syndrome including type 2 diabetes and obesity. Lowering of the plasma levels of glucose, triglycerides, cholesterol, free fatty acids may also be beneficial for the prevention and treatment of atherosclerosis.

It is concluded that treatment with modulators of O/E-1 and/or O/E-2 and/or O/E-3 activity or amount can lead to stimulation of pre-adipocyte differentiation and therefore constitutes a novel treatment for dyslipidemia and insulin resistance syndrome and type 2 diabetes.

Compounds that inhibit the adipocyte differentiating effects of O/E-1 and/or O/E-2 and/or O/E-3 may be useful in the treatment of diseases caused by increased fat accumulation or lipid storage. Examples of such diseases are obesity, osteoporosis, and acne.

This invention provides methods for stimulation or inhibition of pre-adipocyte differentiation comprising the administration of an effective amount of a compound that modulates the activity or amount of O/E-1 and/or O/E-2 and/or O/E-3. Modulation of the amount of O/E-1 and/or O/E-2 and/or O/E-3 by a compound may be brought about for example through altered gene expression level or message stability. Modulation of the activity of O/E-1 by a compound may be brought about for example through compound binding to O/E-1, O/E-1 homodimers or O/E-1-DNA complexes.

In a further aspect of the present invention we provide a method for the provision of an adipocyte differentiation agent, which method comprises using one or several putative modulators of O/E-1 and/or O/E-2 and/or O/E-3 amount or activity as test compounds in one or several procedures to measure the ability of the test compound to modulate O/E-1 and/or O/E-2 and/or O/E-3, and selecting active compounds for use as agents able to stimulate and inhibit pre-adipocyte differentiation, respectively.

Convenient test procedures include the use of animal models to test the role of the test compound. These will typically involve the administration of compounds by intra peritoneal injection, subcutaneous injection, intravenous injection, oral gavage or direct injection via canullae into the blood stream of experimental animals. The effects on insulin sensitivity, lipid profiles, food intake, body temperature, metabolic rate, behavioural activities, body weight and body composition changes may all be measured using standard procedures.

Suitable modulators may be identified by initial screening for modulators of O/E-1 and/or O/E-2 and/or O/E-3 activity or amount against O/E-1 and/or O/E-2 and/or O/E-3 expressing cells or the isolated O/E-1 and/or O/E-2 and/or O/E-3 protein or fragment or chimaeirc form thereof.

Preferably the screening is performed using an assay selected from:
i) measurement of O/E-1 activity using a reporter gene assay comprising a cell line which expresses O/E-1 and a reporter gene coupled to an O/E-1 response element and assaying for expression of the reporter gene.
ii) measurement of O/E-1 activity using purified O/E-1 protein or a fragment thereof, and assaying the interaction between O/E-1 and a DNA fragment, preferably in an electrophoresis mobility shift assay (EMSA).
iii) measurement of O/E-1 activity using purified O/E-1 protein or a fragment thereof and a dimerisation partner or a fragment thereof, and assaying the dimerisation of O/E-1, preferably by time resolved fluorescence resonance energy transfer or by scintillation proximity assay
iv) measurement of O/E-1 transcription or translation in a cell line expressing O/E-1.
v) measurement of direct compound binding or competitive binding to O/E-1, preferably by time resolved fluorescence resonance energy transfer or scintillation proximity assay.

Preferably the screening is performed using an assay selected from:
i) measurement of O/E-2 activity using a reporter gene assay comprising a cell line which expresses O/E-2 and a reporter gene coupled to an O/E-2 response element and assaying for expression of the reporter gene.
ii) measurement of O/E-2 transcription or translation in a cell line expressing O/E-2.

Preferably the screening is performed using an assay selected from:
i) measurement of O/E-3 activity using a reporter gene assay comprising a cell line which expresses O/E-3 and a reporter gene coupled to an O/E-3 response element and assaying for expression of the reporter gene.
ii) measurement of O/E-3 transcription or translation in a cell line expressing O/E-3.

Preferably the cell line is a 3T3-L1 preadipocyte cell, a 3T3-L1 adipocyte cell, a NIH/3T3 fibroblast, or an embryonic fibroblast.

DNA encoding mammalian O/E-1 and/or O/e-2 and/or O/E-3 may be conveniently isolated from commercially available RNA, brain cDNA libraries, genomic DNA, or genomic DNA libraries using conventional molecular biology techniques such as library screening and/or Polymerase Chain Reaction (PCR). These techniques are extensively detailed in Molecular Cloning—A Laboratory Manual, $2^{nd}$ edition, Sambrook, Fritsch & Maniatis, Cold Spring Harbor Press.

The resulting cDNAs encoding mammalian O/E-1s and/or O/e-2s and/or O/E-3s are then cloned into commercially available mammalian expression vectors such as the pcDNA3 series (InVitrogen Ltd etc. see below). An alternative mammalian expression vector is disclosed by Davies et al., J of Pharmacol & Toxicol. Methods, 33, 153-158. Standard transfection technologies are used to introduce these DNA's into commonly available cultured, mammalian cell lines such as CHO, HEK293, HeLa and clonal derivatives expressing the recombinant O/E-1 and/or O/e-2 and/or O/E-3 are isolated. An alternative expression system is the MEL cell expression system claimed in our UK patent no. 2251622.

In addition, these cDNAs may be transfected into derivatives of these cells lines that have previously been transfected with a "reporter" gene. Examples of suitable reporter genes are, but not limited to, esterases, phosphatases, proteases, fluorescent proteins, such as GFP, YFP, BFP, and CFP, luciferase, cloramphenicol acetyl transferase, β-galactosidase, β-glucuronidase. The reporter gene is constructed so as to contain promoter elements that will respond to the activity and amount of O/E-1 and/or O/e-2 and/or O/E-3 in the cell by increased expression of the reporter gene which can be measured by the level of the reporter gene product expressed.

Preferably the protein is human recombinant O/E-1 or mouse recombinant O/E-1. Preferably the protein is mouse recombinant O/E-2 and mouse recombinant O/E-3. The cDNA and amino acid sequence of human and mouse O/E-1 can e.g. be obtained from the EMBL database accession no. AF208502 (human O/E-1) and accession no. L12147 (MMEARLYB) (mouse O/E-1).

These assays may be used to identify low molecular weight compounds that increase the activity or amount of O/E-1 and/or O/e-2 and/or O/E-3; these are defined as "activators".

In addition or alternatively, the same assays can be used to identify low molecular weight compounds that decrease the activity or amount of O/E-1 and/or O/e-2 and/or O/E-3; these are defined as "inhibitors".

The test compound may be a polypeptide of equal to or greater than, 2 amino acids such as up to 6 amino acids, up to 10 or 12 amino acids, up to 20 amino acids or greater than 20 amino acids such as up to 50 amino acids. For drug screening purposes, preferred compounds are chemical compounds of low molecular weight and potential therapeutic agents. They are for example of less than about 1000 Daltons, such as less than 800, 600 or 400 Daltons in weight. If desired the test compound may be a member of a chemical library. This may comprise any convenient number of individual members, for example tens to hundreds to thousands to millions etc., of suitable compounds, for example peptides, peptoids and other oligomeric compounds (cyclic or linear), and template-based smaller molecules, for example benzodiazepines, hydantoins, biaryls, carbocyclic and polycyclic compounds (eg. naphthalenes, phenothiazines, acridines, steroids etc.), carbohydrate and amino acids derivatives, dihydropyridines, benzhydryls and heterocycles (eg. triazines, indoles, thiazolidines etc.). The numbers quoted and the types of compounds listed are illustrative, but not limiting. Preferred chemical libraries comprise chemical compounds of low molecular weight and potential therapeutic agents.

In a further aspect of the invention we provide the use of a modulator of O/E-1 and/or O/e-2 and/or O/E-3 activity or amount as an agent able to stimulate pre-adipocyte differentiation and thereby modify or or prevent atherosclerosis by means of ameliorating the dyslipidemia associated with the insulin resistance syndrome including type 2 diabetes and obesity.

In a further aspect of the present invention we provide a method of treating or preventing atherosclerosis, insulin resistance syndrome, dyslipidemia or type 2 diabetes which method comprises administering to a patient suffering from such a disease a pharmaceutically effective amount of an agent, preferably identified using one or more of the methods of this invention, able to stimulate pre-adipocyte differentiation by modulating O/E-1 and/or O/e-2 and/or O/E-3 activity or amount and thereby modify or ameliorate or prevent the atherosclerosis, insulin resistance syndrome, dyslipidemia or type 2 diabetes disease.

This invention further provides use of a compound able to modulate the activity or amount of O/E-1 and/or O/e-2 and/or O/E-3 in preparation of a medicament for the treatment or prevention of atherosclerosis, dyslipidemia, IRS, and type 2 diabetes. Preferably the compound is an O/E-1 and/or O/e-2 and/or O/E-3 activator.

In a further aspect of the invention we provide the use of a modulator of O/E-1 and/or O/e-2 and/or O/E-3 activity or amount as an agent able to inhibit pre-adipocyte differentiation and thereby modify or ameliorate or prevent obesity.

In a further aspect of the present invention we provide a method of treating or preventing obesity which method comprises administering to a patient suffering from obesity a pharmaceutically effective amount of an agent, preferably identified using one or more of the methods of this invention, able to inhibit pre-adipocyte differentiation by modulating O/E-1 and/or O/e-2 and/or O/E-3 activity or amount and thereby modify or ameliorate or prevent obesity.

This invention further provides use of a compound able to modulate the activity or amount of O/E-1 and/or O/e-2 and/or O/E-3 in preparation of a medicament for the treatment or prevention of obesity. Preferably the compound is an O/E-1 and/or O/e-2 and/or O/E-3 inhibitor.

Modulation of the amount of O/E-1 and/or O/e-2 and/or O/E-3 by a compound may be brought about for example through altered gene expression level or message stability. Modulation of the activity of O/E-1 by a compound may be brought about for example through compound binding to O/E-1 protein. In one embodiment, modulation of O/E-1 comprises a compound able to increase the activity of O/E-1.

According to another aspect of the present invention there is provided a method of preparing a pharmaceutical composition which comprises:
i) identifying a compound as useful for treatment or prevention of atherosclerosis, dyslipidemia, insulin resistance syndrome, type 2 diabetes or obesity according to a method as described herein; and
ii) mixing the compound or a pharmaceutically acceptable salt thereof with a pharmaceutically acceptable excipient or diluent.

The pharmaceutical composition can further comprise a PPARγ agonist, exemplified by, but not limited to, thiazolidinediones, such as, rosiglitazone, and pioglitazone.

It will be appreciated that the present invention includes the use of orthologues and homologues of the human O/E-1 and/or O/e-2 and/or O/E-3. By the term "orthologue" we mean the functionally equivalent O/E-1 and/or O/e-2 and/or O/E-3 in other species. By the term "homologue" we mean a substantially similar and/or related O/E-1 and/or O/e-2 and/or O/E-3 in the same or a different species.

For either of the above definitions we believe the O/E-1s and/or O/e-2s and/or O/E-3s may have for example at least 30%, such as at least 40%, at least 50%, at least 60%, and in particular at least 70%, such as at least 80%, for example 85%, or 90% or 95% peptide sequence identity. It is appreciated that homologous O/E-1s and/or O/e-2 and/or O/E-3 may have substantially higher peptide sequence identity over small regions representing functional domains. We include O/E-1s and/or O/e-2s and/or O/E-3s having greater diversity in their DNA coding sequences than outlined for the above amino acid sequences but which give rise to O/E-1s and/or O/e-2s and/or O/E-3s having peptide sequence identity falling within the above sequence ranges. Convenient versions of the O/E-1 include the published sequences such as EMBL database accession no. AF208502 (human O/E-1) and accession no. L12147 (MMEARLYB) (mouse O/E-1). The O/E-1 is from any mammalian species, including human, monkey, rat, mouse and dog. Preferably the human O/E-1 is used.

Fragments and partial sequences of the O/E-1 and/or O/e-2 and/or O/E-3 may be useful substrates in the assay and analytical methods of the invention. It will be appreciated that the only limitation on these is practical, they must comprise the necessary functional elements for use in the relevant assay and/or analytical procedures.

The agent of this invention may be administered in standard manner for the condition that it is desired to treat, for example by oral, topical, parenteral, buccal, nasal, or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

Knowledge of the O/E-1 and/or O/e-2 and/or O/E-3 also provides the ability to regulate its expression in vivo by for example the use of antisense DNA or RNA. Thus, according to a further aspect of the invention we provide an appetite control agent comprising an antisense DNA or an antisense RNA which is complementary to all or a part of a polynucleotide sequences shown in sequence nos. 1, 3 and 5. By complementary we mean that the two molecules can hybridise to form a double stranded molecule through nucleotide base pair interactions to the exclusion of other molecular interactions.

The antisense DNA or RNA for co-operation with polynucleotide sequence corresponding to all or a part of a O/E-1 and/or O/e-2 and/or O/E-3 gene can be produced using conventional means, by standard molecular biology and/or by chemical synthesis. The antisense DNA or RNA can be complementary to the full length O/E-1 and/or O/e-2 and/or O/E-3 gene of the invention or to a fragment thereof. Antisense molecules which comprise oligomers in the range from about 12 to about 30 nucleotides which are complementary to the regions of the gene which are proximal to, or include, the protein coding region, or a portion thereof, are preferred embodiments of the invention. If desired, the antisense DNA or antisense RNA may be chemically modified so as to prevent degradation in vivo or to facilitate passage through a cell membrane and/or a substance capable of inactivating mRNA, for example ribozyme, may be linked thereto and the invention extends to such constructs.

Oligonucleotides which comprise sequences complementary to and hybridizable to the O/E-1 are contemplated for therapeutic use. U.S. Pat. No. 5,639,595, Identification of Novel Drugs and Reagents, issued Jun. 17, 1997, wherein methods of identifying oligonucleotide sequences that display in vivo activity are thoroughly described, is herein incorporated by reference.

Nucleotide sequences that are complementary to the O/E-1 and/or O/e-2 and/or O/E-3 encoding nucleic acid sequence can be synthesised for antisense therapy. These antisense molecules may be DNA, stable derivatives of DNA such as phosphorothioates or methyiphosphonates, RNA, stable derivatives of RNA such as 2'-O-alkylRNA, or other oligonucleotide mimetics. U.S. Pat. No. 5,652,355, Hybrid Oligonucleotide Phosphorothioates, issued Jul. 29, 1997, and U.S. Pat. No. 5,652,356, Inverted chimeric and Hybrid Oligonucleotides, issued Jul. 29, 1997, which describe the synthesis and effect of physiologically-stable antisense molecules, are incorporated by reference. O/E-1 gene antisense molecules may be introduced into cells by microinjection, liposome encapsulation or by expression from vectors harbouring the antisense sequence.

DESCRIPTION OF THE DRAWINGS

The invention will now be illustrated by the following non-limiting Examples in which.

EXAMPLE 1

Expression of O/E-1 during Adipate Differentiation

Figure 1:
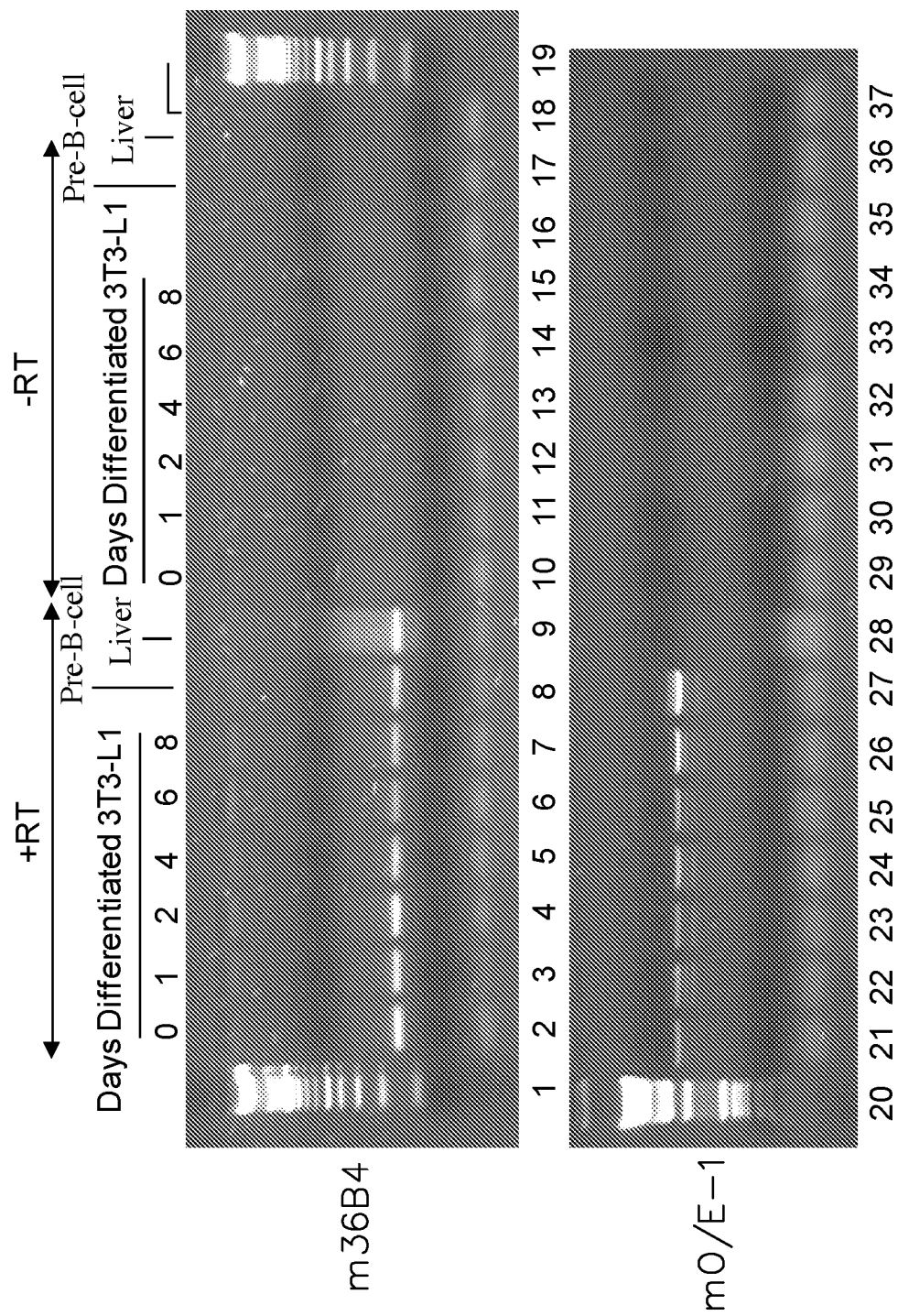
FIG. 1. O/E-1 is expressed already in undifferentiated 3T3-L1 preadipocytes. RT-PCR analysis of O/E-1 levels in mouse 3T3-L1 preadipocytes differentiated for 0, 1, 2, 4, 6 and 8 days using dexamethasone, insulin and isobutylmetylxanthine as inducers, the data shown is after 30 cycles of PCR (lower panel). Mouse 36B4 PCR primers were used for control of cDNA levels, the data shown is after 20 cycles of PCR (upper panel). RNA from mouse 70Z/3 pre-B-cells and liver were used as positive and negative controls for O/E-1 expression. +RT indicates that the cDNA synthesis was performed in the presence of reverse transcriptase while −RT indicates that the cDNA synthesis was performed in the absence of reverse transcriptase.

3T3-L1 preadipocytes (ATCC) were grown to confluence and allowed to differentiate to adipocytes two days post confluence using the adipogenic inducers dexamethasone (1 μM) insulin (1 μg/ml) and isobutylmethylxanthine (0.115 mg/ml) (DIM) for two days and insulin only for two days. RNA was prepared from confluent non-induced cells, and from induced cells at day 1, 2, 4, 6 and 8 post induction. cDNA was prepared and the amount of O/E-1 and 36B4 control transcript was determined by PCR (FIG. 1). Interestingly, O/E-1 was expressed already in uninduced 3T3-L1 cells, indicating that this factor is present early in the adipocyte differentiation program before the onset of other adipogenic factors such as PPARγ and C/EBP (Cowherd et al., 1999). A slight upregulation (3-4 fold) in the O/E-1 transcript levels could also observed during adipocyte differentiation, while no expression could be detected in the liver. (FIG. 1.) These results indicate that O/E-1 is expressed at early stages in adipocyte differentiation and may play important roles for the development of this cell lineage.

EXAMPLE 2

Expression of O/E-1 in Human Adipate Tissue

Figure 2:
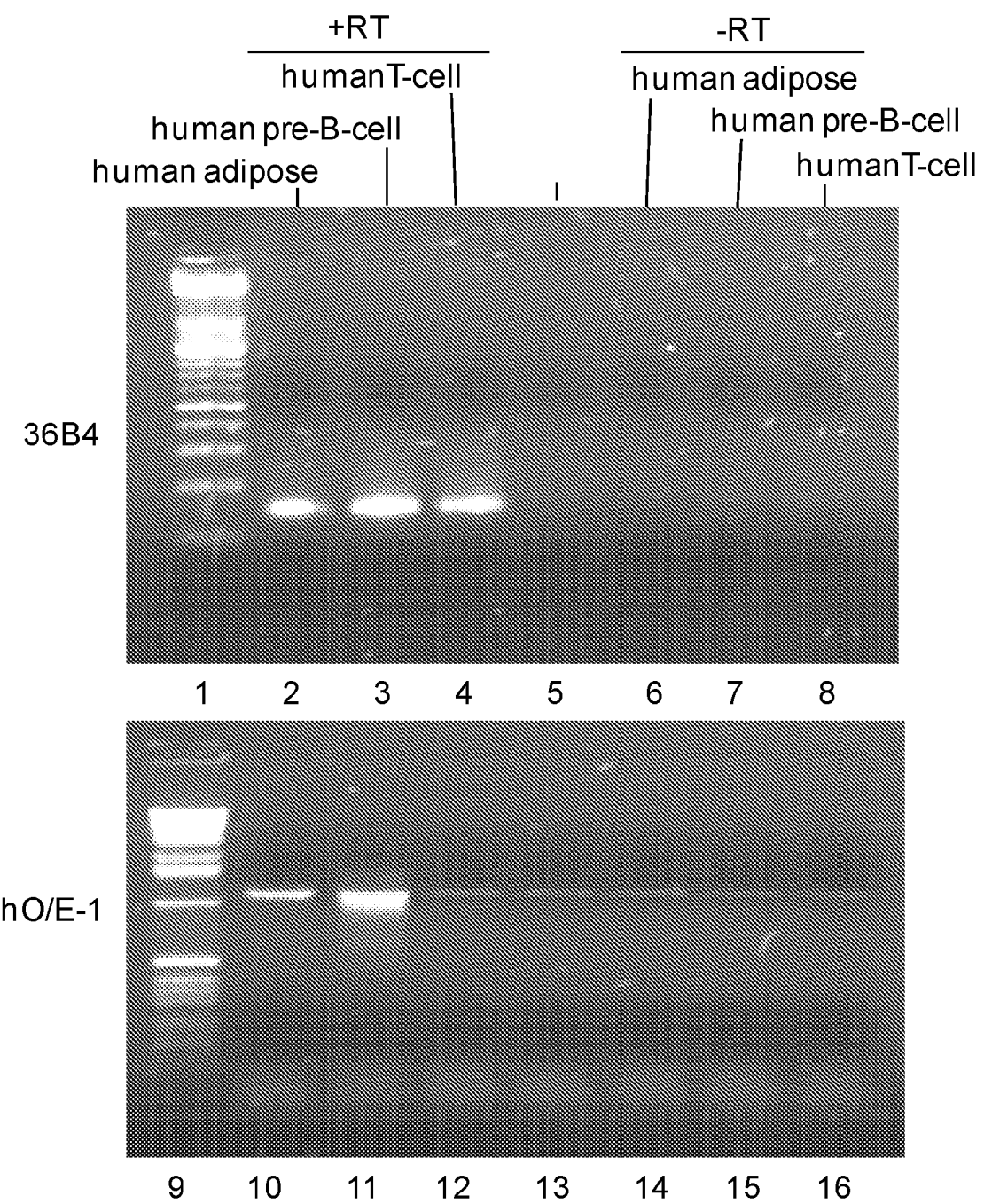
FIG. 2. O/E-1 is expressed in human adipose tissue. RT-PCR analysis of O/E-1 levels in human adipose tissue, data shown is after 35 cycles of PCR (lower panel). 36B4 primers were used for control of cDNA levels, data shown is after 25 cycles of PCR (upper panel). RNA from human Nalm 6 pre-B-cells and Jurkat T-cells were used as positive and negative controls for O/E-1 expression. +RT indicates that the cDNA synthesis was performed in the presence of reverse transcriptase while −RT indicates that the cDNA synthesis was performed in the absence of reverse transcriptase.

All functions of O/E-1 in B-lymphocyte studied so far seem to be conserved between mice and humans, suggesting that the same situation is true also for O/E-1 in adipose tissue. To determine if O/E-1 is expressed in human adipose tissue total RNA was prepared and used as template for cDNA synthesis. As control for O/E-1 expression, cDNAs from human B and T-lymphocytes were also included. O/E-1 and 36B4 control transcript levels were determined by PCR (FIG. 2) and O/E-1 was indeed expressed also in human adipose tissue at levels comparable to those found in human B-lymphocytes, (FIG. 2.) indicating that the role O/E-1 may play in mouse adipose tissue is persevered also in humans.

EXAMPLE 3

Overexpression of O/E-1 by Retroviral Transfer

Figure 3:
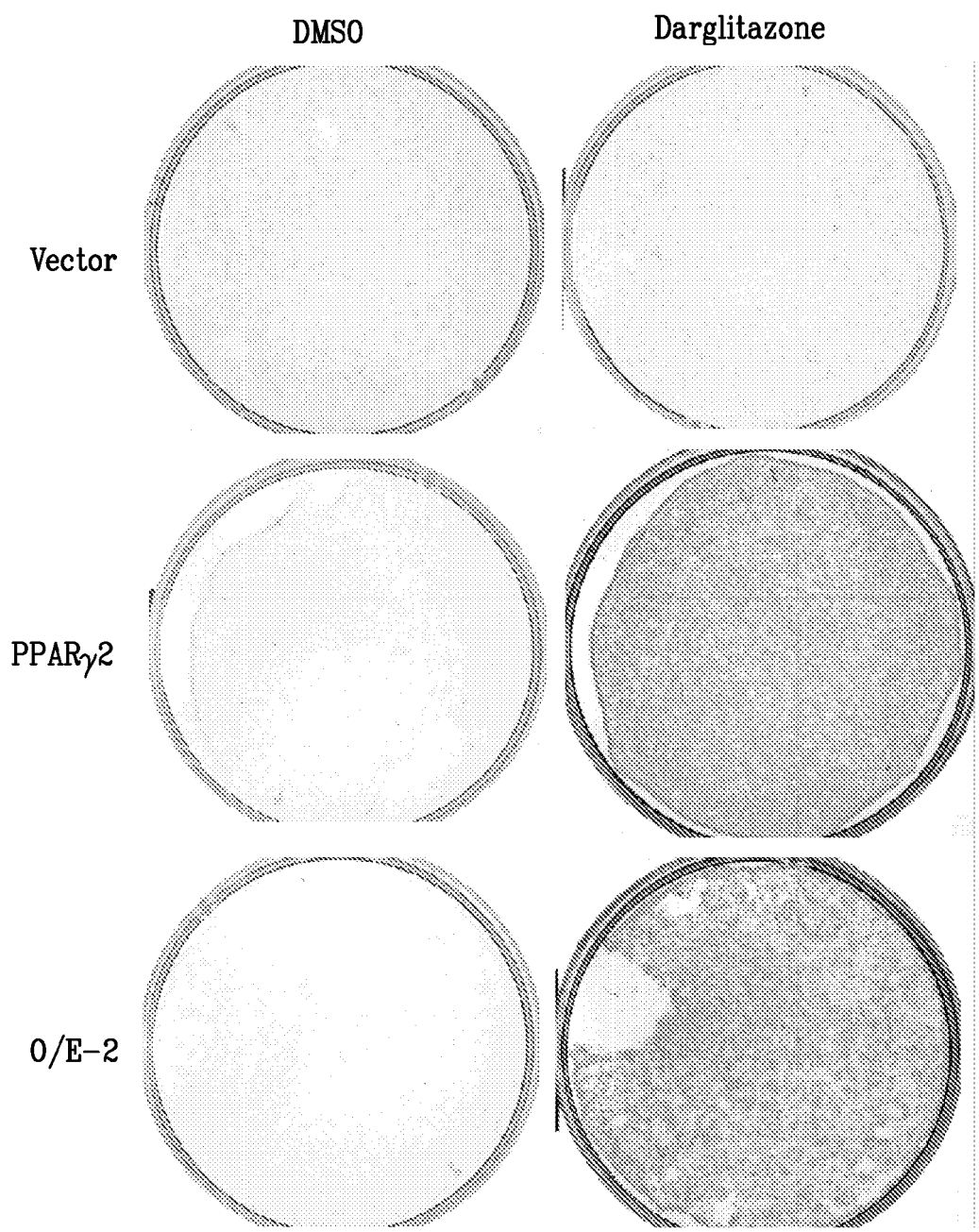
FIG. 3. O/E-1 promotes adipocyte differentiation in uncommitted NIH/3T3 fibroblasts. Differentiation of vector, O/E-1, and PPARγ2 retrovirus infected NIH/3T3 mouse fibroblasts, induced to differentiate using dexamethasone, insulin and isobutylmethylxanthine either in the presence or absence of the PPARγ ligand darglitazone and were stained with Oil Red O after 10 days of differentiation.

A classical way of studying the adipocyte differentiating potential of a gene is to overexpress it in either uncommitted NIH/3T3 fibroblasts or in 3T3-L1 preadipocytes using retroviral transfer. The adipocyte differentiating potential can then be assayed by microscopic examination and by staining with lipophilic dyes such as Oil Red O. O/E-1 was thus expressed in mouse NIH/3T3 fibroblasts, 3T3-L1 preadipocytes and mouse embryonic fibroblasts to investigate its adipocyte differentiating potential. cDNAs encoding mouse O/E-1, human O/E-1 and mouse PPARγ2 were cloned in the pBabepuro retrovirus vector. These retrovirus vectors as well as the empty vector were transiently transfected into Phoenix high efficiency packaging cells. Retroviruses containing supernatants were used to infect NIH/3T3 mouse fibroblasts. After puromycin (2 μg/ml) selection for two days, cells were allowed to grow to confluence after which adipogenic inducers were added (DIM, see above), after 10 days cells were stained with the lipophilic dye Oil Red O. As expected PPARγ induced some differentiation of NIH/3T3 mouse fibroblasts into lipid-containing cells that resembled cultured adipocytes in the presence of adipogenic inducers (FIG. 3). Also as expected a dramatic increase was observed when the high affinity PPARγ ligand darglitazone (0.5 μM) was present throughout the experiment in combination with the adipogenic inducers. No differentiation was observed in NIH/3T3 vector infected cells treated with adipogenic inducers either in the presence or absence of darglitazone. Surprisingly NIH/3T3 cells infected with mouse O/E-1 development to adipocytes at a similar rate as PPARγ2 infected cells and this process was also greatly enhanced when darglitazone was present, suggesting that O/E-1 is involved in controlling adipocyte differentiation (FIG. 3). The ability of human O/E-1 to induce adipocyte differentiation of NIH/3T3 was also tested and found to be similar as that of mouse O/E-1 (Data not shown).

Figure 4A:
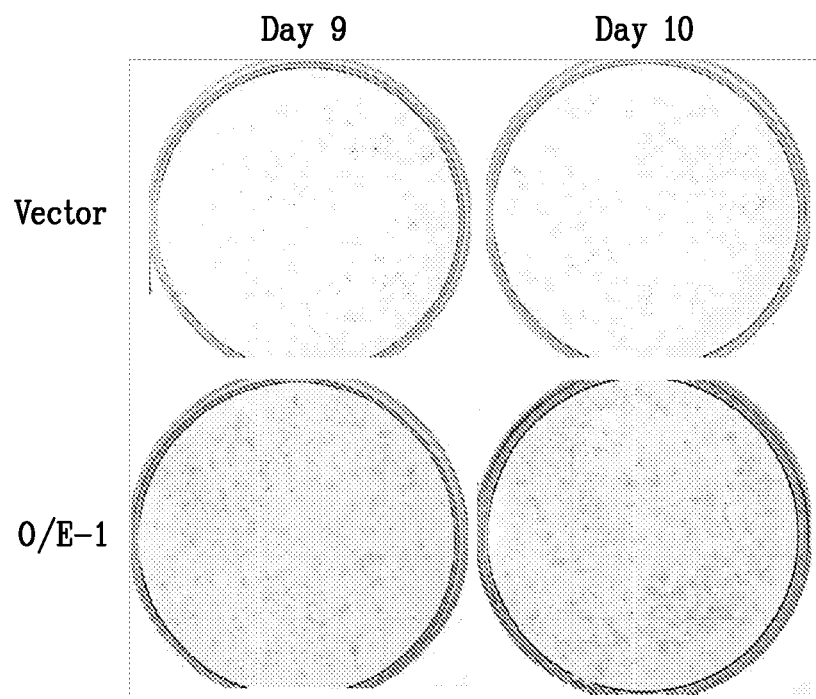
FIG. 4. O/E-1 increases the rate of differentiation in 3T3-L1 preadipocytes. Differentiation of vector and O/E-1 infected 3T3-L1 preadipocytes. A. Infected cells induced with dexamethasone only stained with Oil Red O after indicated days of differentiation. B. Infected cells induced with dexamethasone and the PPARγ ligand darglitazone Oil Red O stained after indicated days of differentiation.
Figure 4B:
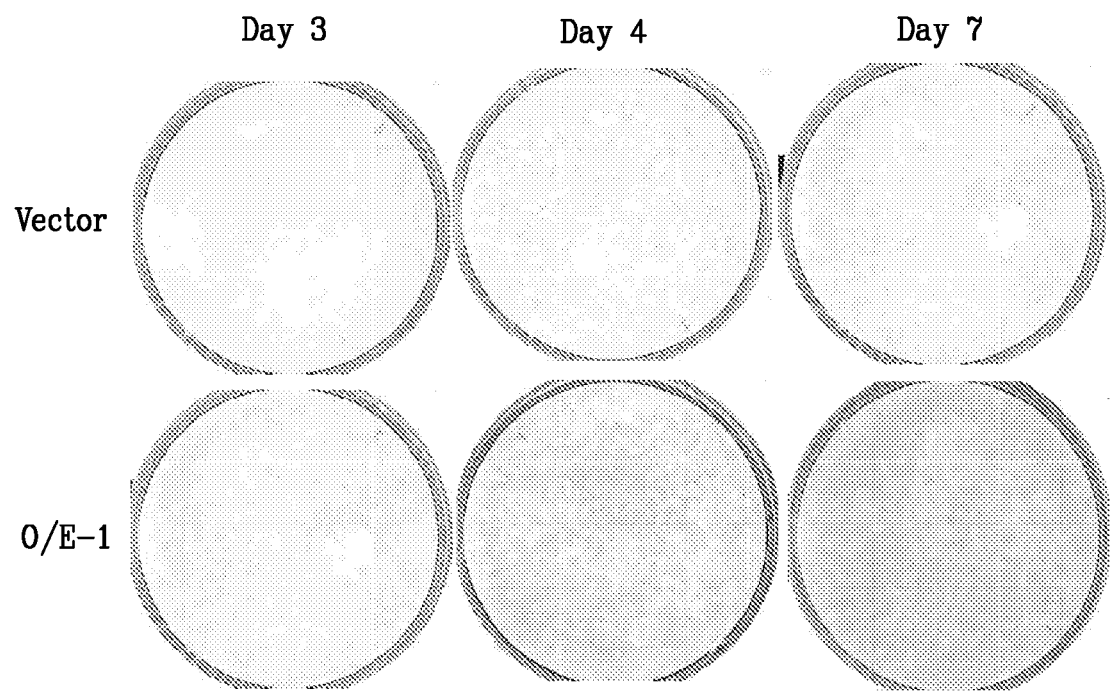
Figure 5:
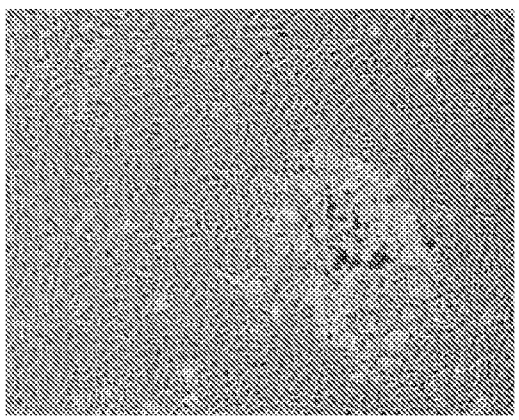
FIG. 5. O/E-1 enhances the rate of differentiation in untransformed mouse embryonic fibroblasts (MEF). Cells were infected with vector or O/E-1 retrovirus and induced to differentiate with dexamethasone, insulin, isobutylmethylxanthine and the PPARγ ligand darglitazone and stained with Oil Red O after 10 days.
Figure 5:
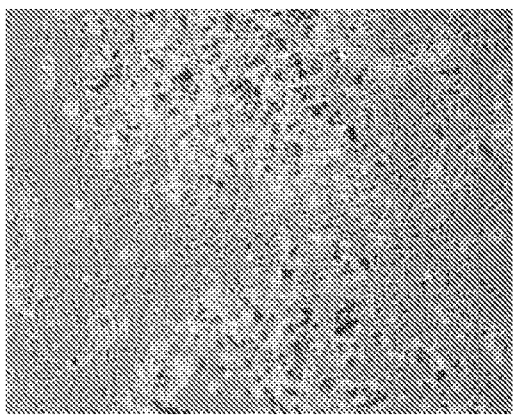
Figure 5:
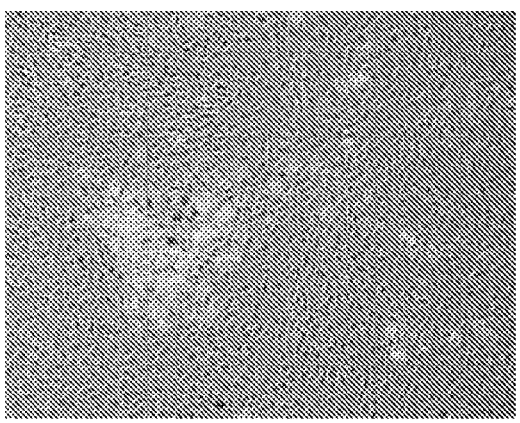
Figure 5:
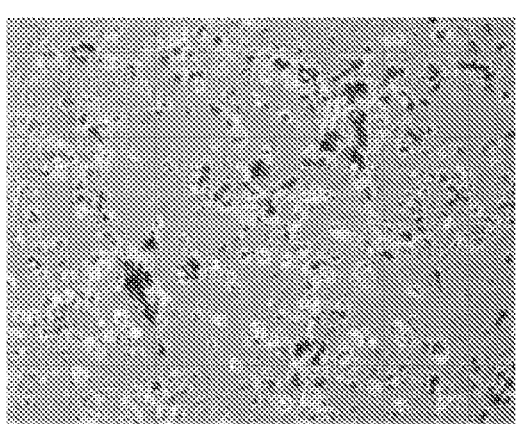
Figure 5:
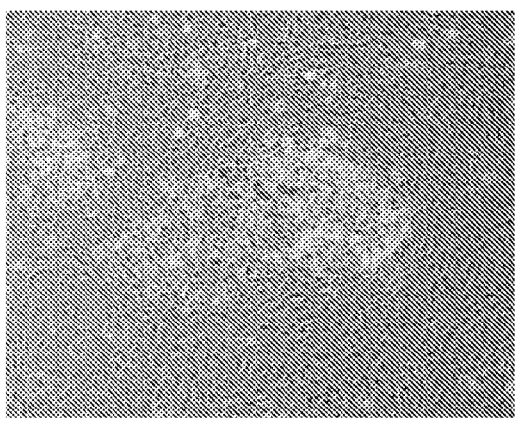
Figure 5:
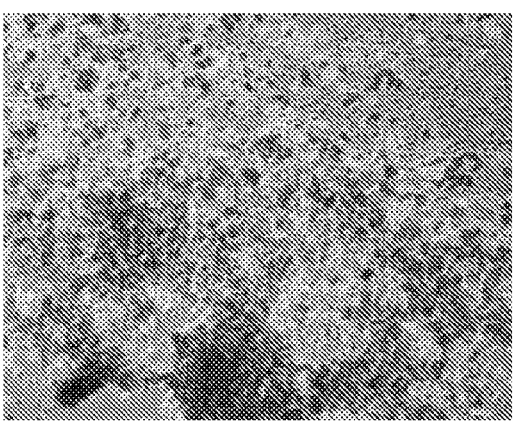

The fibroblastic 3T3-L1 preadipocyte cells have the capability to differentiate to adipocytes when given the proper hormonal stimulation, usually a combination of dexamethasone, insulin and isobutylmethylxanthine, as opposed to NIH/3T3 where overexpression of adipocyte differentiating factors is necessary to get adipocyte development. Untransformed mouse embryonic fibroblasts (MEF) can also be forced to adipocyte differentiation using the same adipogenic factors; the efficiency is however much lower than with 3T3-L1. To show that the capability of O/E-1 to stimulate adipocyte differentiation was not specific for one particular cell line, O/E-1 was over expressed using retrovirus mediated transfer in 3T3-L1 and MEF. Stable clones were selected 2-3 days using puromycin (2 μg/ml) and surviving cells were grown to confluence. 3T3-L1 cells differentiate to adipocytes at high rate when all adipogenic inducers are present and this could make it difficult discriminate the effect of an additional adipogenic signal. The cells were therefore induced with dexamethasone (1 μM) alone for two days or in combination with darglitazone (0.5 μM) throughout the experiment to get a low differentiation rate. MEF on the other hand develop into adipocytes quite inefficiently and were thus induced with the more powerful adipogenic combination of dexamethasone (1 μM), insulin (5 μg/ml) isobutylmethylxanthine (0.115 mg/ml) and darglitazone (0.5 μM) for two days, insulin and darglitazone for two days and darglitazone alone all through the experiment. O/E-1, or vector infected 3T3-L1 preadipocytes were stained with Oil Red O at day 9 and 10 post induction (FIG. 4A) and the rate of adipocyte differentiation was clearly enhanced by O/E-1 under these very slow differentiation conditions. When darglitazone was added in combination with dexamethasone the overall rate of differentiation was enhanced and the cells were stained at day 3, 4 and 7. At day 4 and 7 the O/E-1 infected cultures contained far more adipocytes than vector infected cultures (FIG. 4B). The same pattern could also be observed in MEFs where some differentiation into adipocytes could be observed 10 days post induction in vector infected cultures, the adipocyte like cells grew in many small clusters of 20-50 cells (FIG. 5). A dramatic difference was observed in O/E-1 infected cultures where many cells in large clusters showed Oil Red O staining.

EXAMPLE 4

Assays for Measuring O/E-1 Activity

Mutagenesis of the DNA binding motif of O/E-1 indicate that several histidines and cysteins are important for DNA binding and that these amino acids could represent a loop that is stabilized by a central divalent metal cation (Hagman et al., 1995). Renaturation of denatured O/E-1 polypeptides in the presence of various divalent cations did also show that DNA binding to a $^{32}P$ labeled probe in electrophoretic mobility shift assay (EMSA) was dependent upon inclusion of $Zn^{2+}$ ions. DNA binding could also be achieved in the presence of $Cd^{2+}$ and to a lesser extent by inclusion of $Mg^{2+}$ ions (Hagman et al., 1995) suggesting that other ions could displace $Zn^{2+}$ in vitro. The O/E-1 amino acid sequence can not be aligned with consensus metal binding motifs like zinc fingers indicating that O/E-1 harbors a unique metal containing DNA binding motif that mediates DNA interaction. This unique domain of O/E-1 could be a possible target for modulation of the DNA binding capability of the protein. Relative high concentration $Zn^{2+}$ is needed in vitro to achieve optimal O/E-1 DNA binding (1-10 μM) suggesting that this may be a limiting factor for DNA binding in vivo. Development of high affinity low molecular weight compounds could thus be an attractive way of modulating the O/E-1 activity and adipocyte differentiation. Recombinant, truncated O/E-1 protein containing the DNA binding and dimerization domains can be used in EMSA. Using a protein binding buffer devoid of $Zn^{2+}$ ions, which gives very poor binding to natural O/E-1 DNA binding sites, can be used for testing low molecular weight compounds for modulation, especially stimulation of DNA binding capacity of O/E-1 in EMSA. Using a protein binding buffer with physiological, or close to physiological concentration of $Zn^{2+}$ ions, which gives effective binding to natural O/E-1 DNA binding sites, can be used for testing low molecular weight compounds for modulation, especially inhibition of DNA binding capacity of O/E-1 in EMSA. To increase the throughput other assays based on fluorescence energy transfer for measuring O/E-1 binding to its DNA target site can be developed. Compounds isolated based on their capacity to modulate O/E-1 DNA binding can be tested further in cell based assays using reporter constructs containing natural DNA binding sites. Selected compounds with activities in binding and reporter assays can be tested for activity in adipocyte differentiation models based on preadipocyte cell lines.

EXAMPLE 5

Overexpression of Human O/E-1 in MEF

Figure 6:
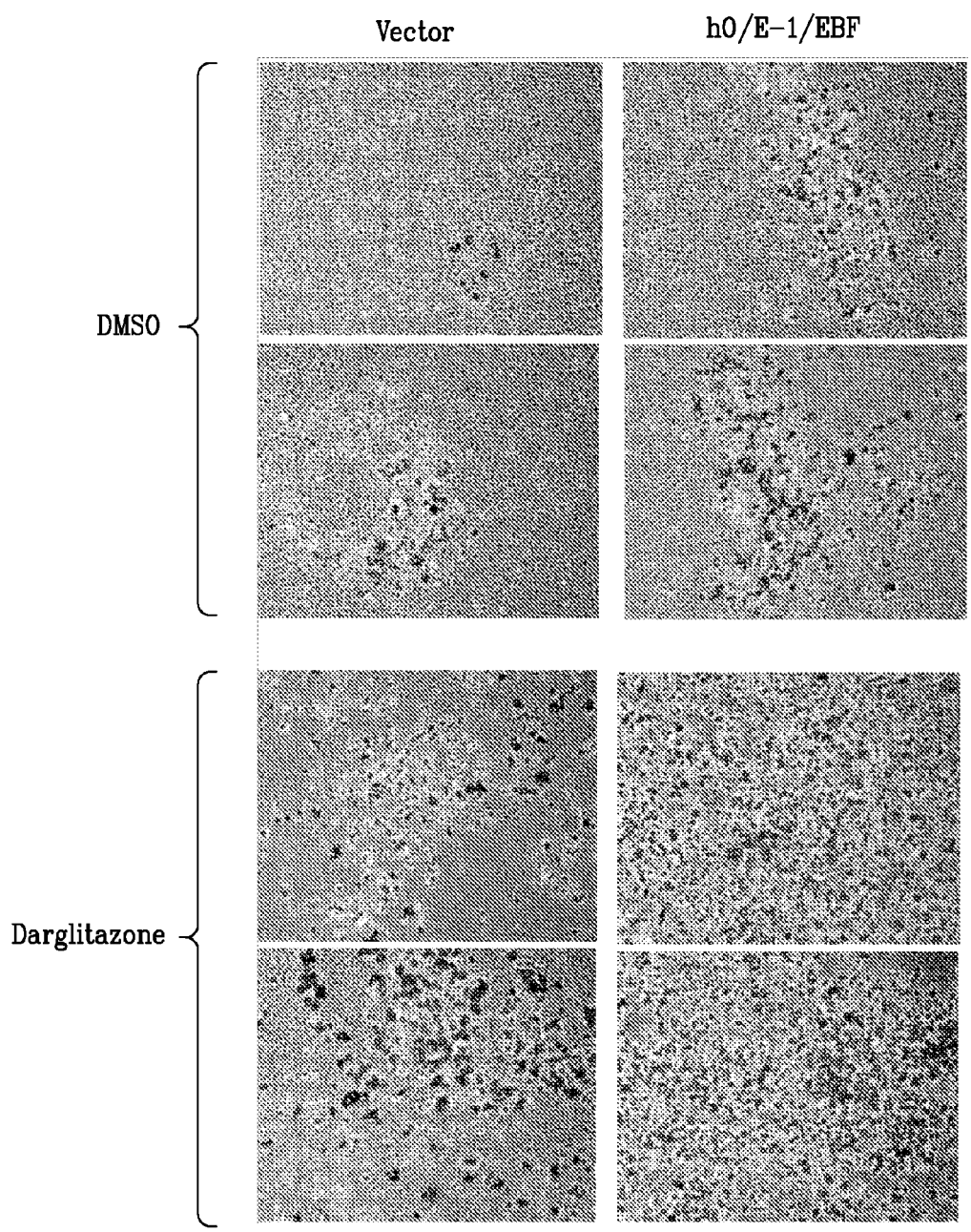
FIG. 6. The ability of human O/E-1 to stimulate adipocyte differentiation was tested in MEF. Duplicate dishes with cells infected with vector or human O/E-1 were induced to differentiate as described in example 3, with or without darglitazone present.

The ability of human O/E-1 to stimulate adipocyte differentiation was tested in MEF. Duplicate dishes with cells infected with vector or human O/E-1 were induced to differentiate as described in example 3, with or without darglitazone present (FIG. 6). At day 13 post-induction adipate differentiation was measured by Oil Red O staining. Vector infected cells differentiated to adipocytes with low efficiency when treated with vehicle. As expected, the addition of darglitazone increased the number of cells that developed into adipocytes. Cultures infected with human O/E-1 did, analogues to mouse O/E-1, show increased number of adipocytes compared to vector infected cultures even in the absence of darglitazone. As observed with mouse O/E-1, cultures infected with human O/E-1 showed even further enhanced differentiation when darglitazone was present. These results indicate that mouse and human O/E-1 have a similar capacity to promote adipocyte differentiation.

EXAMPLE 6

Expression of O/E-1, O/E-2 and O/E-3 in Adipose Tissue, Liver, B-Lymphoid Cell Lines and Differentiated 3T3-L1 Preadipocytes Total RNA was isolated from mouse visceral adipose tissue, liver and the 70Z/3 B-lymphoid cell line using RNA STAT-60 (BioSite) according to the manufacturer's instructions. DNA was removed from RNA preparations (DNA-free Kit, Ambion) and first-strand synthesis was performed using random primers (Superscript First-Strand Synthesis System for RT-PCR, Gibco BRL). Transcript levels of O/E-1, -2, and 3 were analyzed by real-time PCR using a ready-to-use assay based on the Taqman technology (PE Applied Biosystems, Weiterstadt, Germany). Fluorescent SYBER-Green was used for detection. 36B4 mRNA was used to calculate $2^{-\Delta Ct}$ values.

Figure 7A:
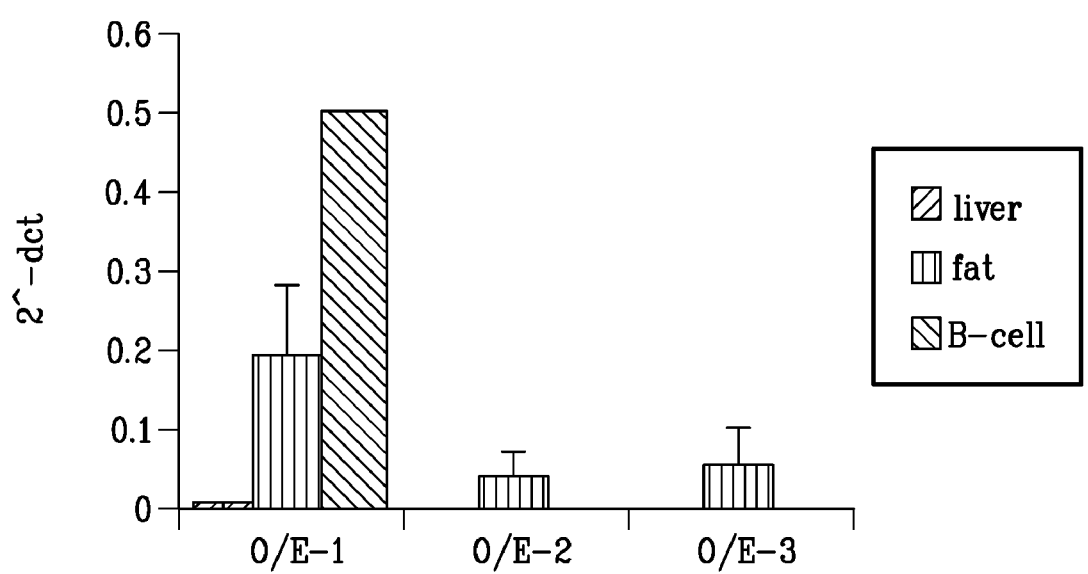
FIG. 7. Expression levels of O/E-1, O/E-2 and O/E-3 transcription factors and markers of adipate differentiation in adipose tissue, liver, B-lymphoid cell lines (A) and differentiated 3T3-L1 preadipocytes (B).

Real-time PCR analysis using primers for O/E-1, -2, and -3 on cDNAs derived from mouse adipose tissue, liver and the 70Z/3 B-lymphoid cell line revealed that all three isoforms of O/E are expressed in mouse adipose tissue, although at different levels with O/E-1 being most abundant (FIG. 7A). Consistent with work reported by others, O/E-1 was the only O/E gene expressed in B-lymphoid cells, while the liver was negative for all isoforms.

3T3-L1 preadipocytes were cultured and induced to differentiate to adipocytes using dexamethasone, insulin, and isobutylmethylxanthine at day 0. RNA was extracted from cultures at preconfluence (p.c), confluence (c), and day 1, 2, 4, 6 and 8 (d1-d8) post induction. DNase treated RNA samples were used as templates in cDNA synthesis, which were used to determine expression levels of O/E-1, -2,-3, PPARγ1 and 2, SREBP1, C/EBPα, aP2 and GPDH by real-time PCR. 36B4 mRNA was used to calculate $2^{-\Delta Ct}$ values.

Figure 7B:
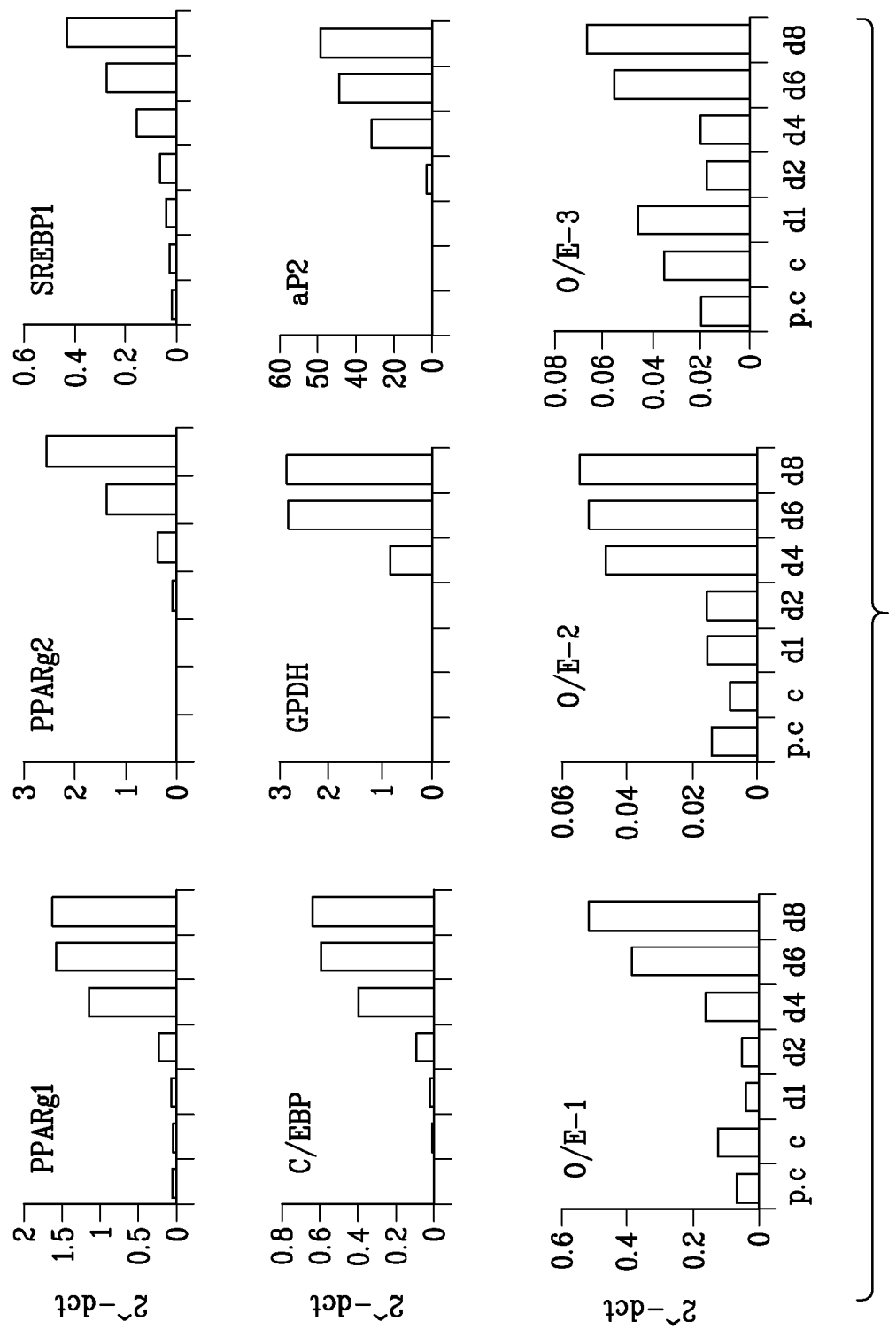

Next, the 3T3-L1 model system for adipocyte differentiation was used to determine at which stage during adipocyte development O/E gene expression of was initiated, and if expression was regulated during the coarse of differentiation. 3T3-L1 preadipocytes were grown to confluence and allowed to differentiate to adipocytes two days post confluence using the adipogenic inducers dexamethasone (1 μM) insulin (1 μg/ml) and isobutylmethylxanthine (0.5 mM) (DIM) for two days and insulin only for two additional days. mRNA levels for O/E-1, 2 and 3, as well as for known markers of adipocyte differentiation, were determined by real-time PCR (FIG. 7B). All O/E-forms were expressed already in uninduced preconfluent 3T3-L1 cells, indicating that these factors are present at early stages of adipocyte development. O/E-2 and 3 were however present at lower levels than O/E-1, which is coherent with the pattern observed in mouse adipose tissue. During 3T3-L1 differentiation O/E-1 was upregulated approximately 8 fold and this tendency could also be observed with the other isoforms although the upregulation was only 2-3 fold. To compare the expression pattern of the O/Es with known markers of adipocyte development we measured mRNA levels of PPARγ1, PPARγ2, SREBP1, C/EBPα, aP2 and GPDH by real-time PCR (FIG. 7B). This analysis showed that the O/Es were expressed at an early stage when low levels of SREBP and PPARγ1 are detected but before the onset of C/EBPα and PPARγ2. These results indicates that O/E-1 mRNA levels are modulated during adipogenesis with a profile similar to those of PPARγ1 and SREBP1.

| Real-time PCR analysis oligonucleotides | |
|---|---|
| Forward oligo | Reverse oligo |
| SEQ ID NO: 1 | SEQ ID NO: 2 |
| SEQ ID NO: 3 | SEQ ID NO: 4 |
| SEQ ID NO: 5 | SEQ ID NO: 6 |
| SEQ ID NO: 7 | SEQ ID NO: 8 |
| SEQ ID NO: 9 | SEQ ID NO: 10 |
| SEQ ID NO: 11 | SEQ ID NO: 12 |
| SEQ ID NO: 13 | SEQ ID NO: 14 |
| SEQ ID NO: 15 | SEQ ID NO: 16 |
| SEQ ID NO: 17 | SEQ ID NO: 18 |
| SEQ ID NO: 19 | SEQ ID NO: 20 |

Figure 8:
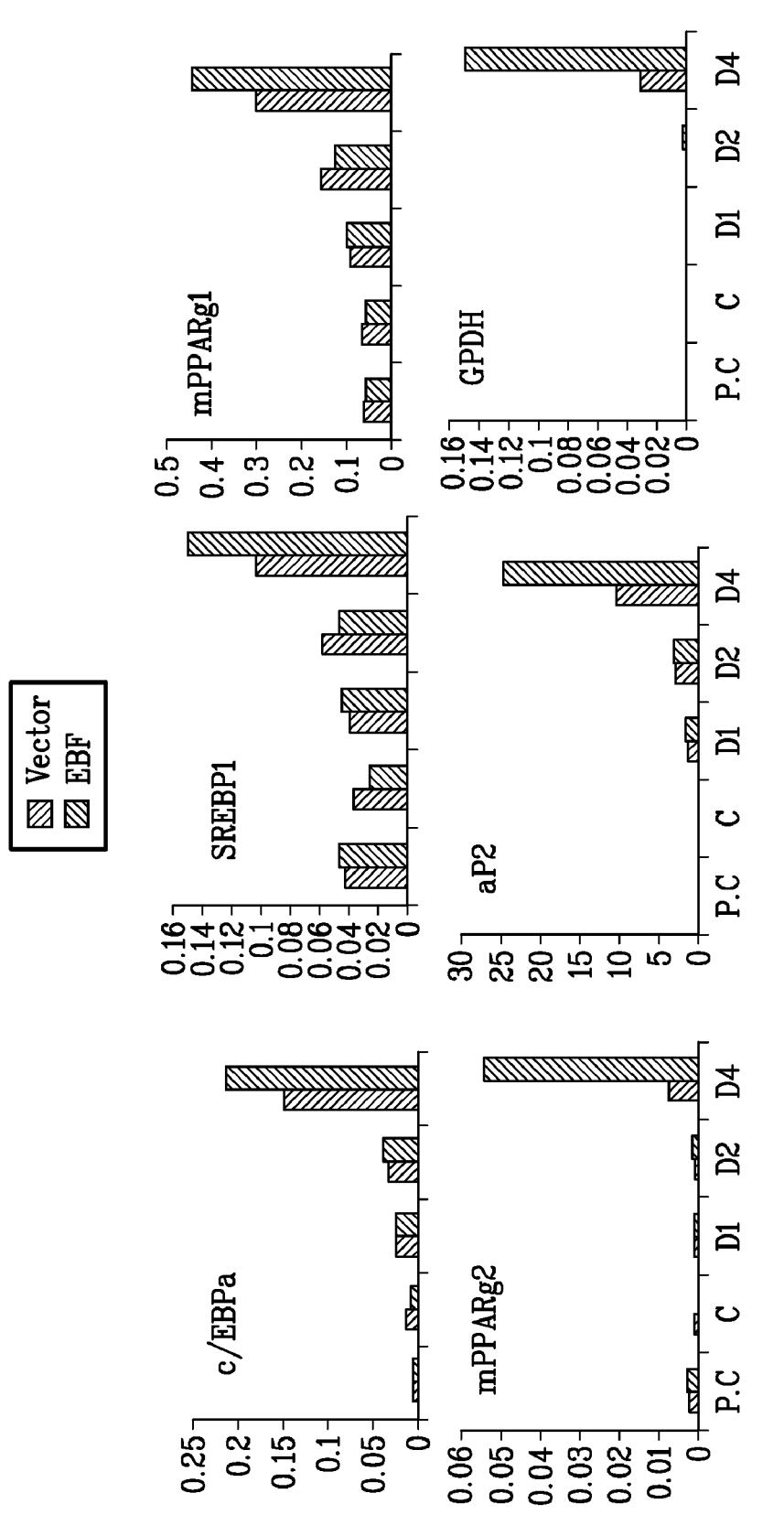
FIG. 8. mRNA levels of markers for adipocyte differentiation in vector and O/E-1 infected cultures. Total RNA was extracted from cultures at preconfluence (p.c), confluence (c), day 1, 2 and 4 (d1-d4) post induction. After Dnase treatment and cDNA synthesis mRNA levels was determined by real-time PCR. 36B4 mRNA was used to calculate $2^{-\Delta Ct}$ values.

EXAMPLE 7 mRNA Levels of Markers for Adipocye Differentiation in Vector and O/E-1 Infected Cells To study the mechanism behind the adipogenic potential of O/E-1, real-time PCR was performed on cDNAs derived from 3T3-L1 cells infected with vector or O/E-1 retroviruses collected at various time-points during dexamethasone (1 μM) and darglitazone (0.5 μM) stimulated differentiation (FIG. 8). At early stages during differentiation, we observed no significant changes in mRNA levels of any of the studied adipocyte differentiation marker genes. By day four-post induction there was, however, a clear up regulation of most of the marker genes in O/E-1 infected cultures, implying that O/E-1 is not directly controlling any of the examined genes. The upregulation of these genes at later stages is likely due to a more efficient differentiation of O/E-1 infected cells.

EXAMPLE 8

O/E-1, -2 and -3 Gene Expression is Regulated in Lean and Obese Mice

Figure 9:
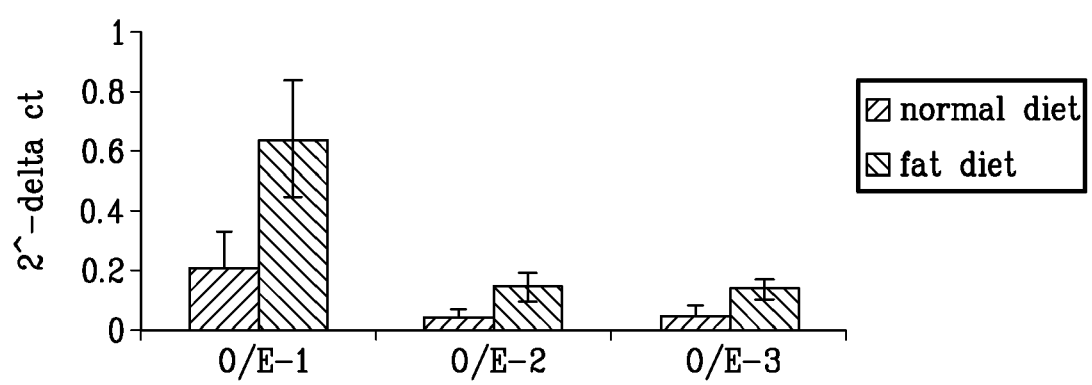
FIG. 9. O/E-1, -2 and -3 gene expression is regulated in lean and obese mice.
Figure 10:
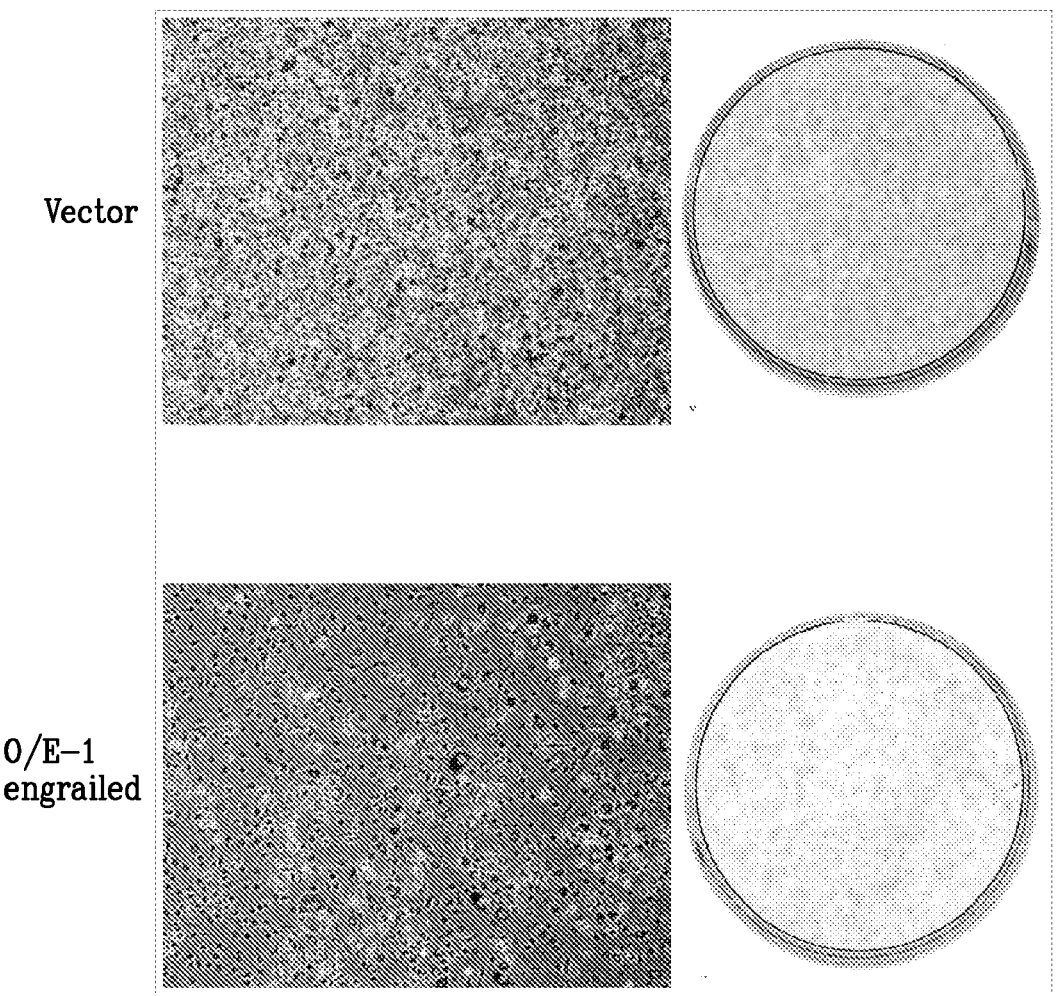
FIG. 10. A dominant negative form of O/E-1 reduces adipogenesis in vitro. 3T3-L1 preadipocytes were infected with a retrovirus vector alone or retroviruses harboring a dominant negative form of O/E-1 where a truncated cDNA, encoding only the DNA-binding domain of O/E-1, was fused to the repressor domain of engrailed. After puromycin selection cells were induced to adipocyte differentiation by dexamethasone, insulin and 3-isobutyl-1-methylxanthine two days post confluence. Adipogeneis was assessed by Oil Red O staining 5 days post induction. Petri dishes (60 mm) and micrographs are shown.

O/E-1, -2 and -3 gene expression is regulated in lean and obese mice. 9-10 wk C57/BL6 mice were fed a standard laboratory rodent chow or chow plus unlimited access to cafeteria diet for 11 wk. High gainers were separated from low gainers by the weight they gained. Five high gainers were compared with five mice that were fed a standard diet. Mouse visceral adipose tissue was isolated and total RNA was extracted and treated with DNase. O/E-1, -2 and -3 mRNA levels were determined by real-time RT-PCR 36B4 mRNA was used to calculate $2^{-\Delta Ct}$ values (FIG. 9).

EXAMPLE 9

A Dominant Negative Form of O/E-1 Reduces Adipogenesis In Vitro

If the O/E proteins are important for adipocyte differentiation it should be possible to reduce differentiation of 3T3-L1 by over expression of a dominant negative form of O/E-1. This would also affect the function of all three O/E proteins since they are reported to interact with the same consensus DNA-binding site (A. Travis, J. Hagman, L. Hwang, R. Grosschedl, *Mol. Cell. Biol.* 13, 3392-3400 (1993); J. Hagman, M. J. Gutch, H. Lin, R. Grosschedl, *Embo J* 14, 2907-16 (1995). Constructing a dominant negative form of the O/E-1 protein is complicated by the fact that this transcription factor has a second transactivating domain within the DNA-binding domain. To overcome this problem we fused the repressor domain of engrailed (amino acids 1-298) with a truncated O/E-1 cDNA lacking the C-terminal transactivation domain while retaining the DNA-binding and dimerization domains (M. Sigvardsson, *Mol Cell Biol* 20, 3640-54. (2000). Retroviruses carrying O/E-1-engrailed were used to infect 3T3-L1 cells and the differentiation capability was compared with vector infected cells. Differentiation was induced with Dexamethasone (1 μM), 3-isobutyl-1-methylxanthine (0.5 mM) and Insulin (1 μg/ml) and cultures were stained with Oil Red O after 5 days. As shown in FIG. 7, over expression of the dominant negative form of O/E-1 in 3T3-L1 cells reduced the capacity of these cells to develop into adipocytes. There was not an absolute block of differentiation in O/E-1-engrailed infected cultures because some cells still accumulated lipids but the number of differentiating cells was reduced. These data indicate that O/E target genes are important and required for differentiation of 3T3-L1 preadipocytes into adipocytes.

The invention claimed is:

1. A method for identifying a compound which modulates pre-adipocyte differentiation comprising testing whether the compound modulates the activity and/or amount of O/E-1 and/or O/E-2 and/or O/E-3.

2. A method according to claim 1, comprising testing whether the compound modulates the activity and/or amount of O/E-1.

3. A method according to claim 1, comprising testing whether the compound modulates the activity and/or amount of O/E-2.

4. A method according to claim 1, comprising testing whether the compound modulates the activity and/or amount of O/E-3.

5. A method according claim 2, in which the test is independently selected from:
   i) measurement of O/E-1 activity using a reporter gene assay comprising a cell line which expresses O/E-1 and a reporter gene coupled to an O/E-1 response element and assaying for expression of the reporter gene;
   ii) measurement of O/E-1 activity using purified O/E-1 protein or a fragment thereof, and assaying the interaction between O/E-1 and a DNA fragment;
   iii) measurement of O/E-1 activity using purified O/E-1 protein or a fragment thereof and a dimerisation partner or a fragment thereof, and assaying the dimerisation of O/E-1; and
   iv) measurement of O/E-1 transcription or translation in a cell line expressing O/E-1,
   v) measurement of direct compound binding or competitive binding to O/E-1.

6. A method according to claim 5, in which measurement of O/E-1 activity using purified O/E-1 protein or a fragment thereof, and assaying the interaction between O/E-1 and a DNA fragment uses an electrophoresis mobility shift assay (EMSA).

7. A method according to claim 5, in which measurement of O/E-1 activity using purified O/E-1 protein or a fragment thereof and a dimerisation partner or a fragment thereof, and assaying the dimerisation of O/E-1 using time resolved fluorescence resonance energy transfer or scintillation proximity assay.

8. A method according to claim 5, in which the cell line is independently selected from a 3T3-L1 preadipocyte cell, a 3T3-L1 adipocytes cell, a NIH/3T3 fibroblast, or an embryonic fibroblast.

9. A method according to claim 5, in which the O/E-1 protein is human recombinant O/E-1 or mouse recombinant O/E-1.

10. A method according to claim 3, in which the test is independently selected from:
    i) measurement of O/E-2 activity using a reporter gene assay comprising a cell line which expresses O/E-2 and a reporter gene coupled to an O/E-2 response element and assaying for expression of the reporter gene; and
    ii) measurement of O/E-2 transcription or translation in a cell line expressing O/E-2.

11. A method according to claim 4, in which the test is independently selected from:
    i) measurement of O/E-3 activity using a reporter gene assay comprising a cell line which expresses O/E-3 and a reporter gene coupled to an O/E-3 response element and assaying for expression of the reporter gene; and
    ii) measurement of O/E-3 transcription or translation in a cell line expressing O/E-3.

12. A method according to claim 10 or 11, in which the cell line is independently selected from a 3T3-L1 preadipocyte cell or a 3T3-L1 adipocytes cell.

13. A method according claim 10 or 11, in which the O/E-2 protein is mouse recombinant O/E-2 and the O/E-3 protein is mouse recombinant O/E-3.

14. A method according to claim 5, in which direct compound binding or competitive binding to O/E-1 is measured by time resolved fluorescence resonance energy transfer or scintillation proximity assay.

* * * * *